(12) United States Patent
Detzler et al.

(10) Patent No.: US 10,521,720 B2
(45) Date of Patent: Dec. 31, 2019

(54) MONITORING UNIT FOR THE ELECTRONIC MONITORING OF SENSOR SIGNALS WITHIN THE FRAMEWORK OF THE MONITORING OF SEPSIS AND A CORRESPONDING PROCESS

(71) Applicant: Dräger Medical GmbH, Luebeck (DE)

(72) Inventors: David Detzler, Berlin (DE); Desislava Nikolova, Hamburg (DE); Petra Schiwiaka, Luebeck (DE); Hannes Schulz, Luebeck (DE); Carsten Wasner, Techau (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 851 days.

(21) Appl. No.: 14/624,785

(22) Filed: Feb. 18, 2015

(65) Prior Publication Data
US 2015/0234993 A1    Aug. 20, 2015

(30) Foreign Application Priority Data
Feb. 19, 2014    (DE) .................. 10 2014 002 172

(51) Int. Cl.
*G06N 5/00* (2006.01)
*G16H 40/63* (2018.01)
*G16H 50/20* (2018.01)

(52) U.S. Cl.
CPC ............... *G06N 5/00* (2013.01); *G16H 40/63* (2018.01); *G16H 50/20* (2018.01)

(58) Field of Classification Search
CPC ..................................................... G06N 5/00
USPC ......................................................... 702/19
See application file for complete search history.

(56) References Cited

U.S. PATENT DOCUMENTS

| 7,022,070 B2 * | 4/2006 | Ebner | ................. | A61B 5/0002 |
| | | | | 600/301 |
| 8,439,835 B1 | 5/2013 | McKinley et al. | | |
| 2003/0036683 A1 | 2/2003 | Kehr et al. | | |
| 2008/0091088 A1 | 4/2008 | Kiani | | |
| 2009/0069642 A1 | 3/2009 | Gao et al. | | |
| 2010/0010319 A1 | 1/2010 | Tivig et al. | | |
| 2010/0113891 A1 | 5/2010 | Barrett et al. | | |
| 2011/0137852 A1 | 6/2011 | Gajic et al. | | |
| 2011/0178376 A1 | 7/2011 | Judy et al. | | |
| 2012/0053422 A1 | 3/2012 | Rantala | | |
| 2013/0265327 A1 * | 10/2013 | Vann | .................... | G06F 19/3406 |
| | | | | 345/629 |
| 2013/0271283 A1 * | 10/2013 | Judy | .................. | G06F 19/3418 |
| | | | | 340/573.4 |
| 2016/0040233 A1 * | 2/2016 | Shi | ......................... | G01N 33/92 |
| | | | | 435/6.12 |

FOREIGN PATENT DOCUMENTS

| CN | 102106757 A | 6/2011 |
| CN | 102375933 A | 3/2012 |
| WO | 2005/124511 A2 | 12/2005 |

OTHER PUBLICATIONS

Reinhart et al., Prävention, Diagnose, Therapie and Nachsorge der Sepsis.

* cited by examiner

*Primary Examiner* — Jerry Lin
(74) *Attorney, Agent, or Firm* — McGlew and Tuttle, P.C.

(57) ABSTRACT

A electronic sensor signals monitoring unit (10), system and computer program, for sepsis monitoring, includes an interactive visualization status calculation monitor (M), a sensor data acquisition interface (11), acquiring time-critical status-relevant sensor signals from medical devices (G), a rule engine interface (12) to a memory or a data bank (DB) with stored rules for analyzing and processing status-relevant parameters and/or sensor signals, and a computer-assisted control unit (S), configured to dynamically control the interactive visualization on the monitor (M) and including an arithmetic unit (RW). The arithmetic unit (RW) is supplied with the acquired sensor signals via the sensor data acquisition interface (11) and is intended for the status calculation with the rules stored in the data bank (DB). The status calculation includes an overview display, a detail view and a logbook view. A display of the course of status-relevant sensor signals over time is visualized in the detail view.

19 Claims, 14 Drawing Sheets

FIG. 3A

Smart Guard Sepsis 1.0 - Patients List

| View | | Show Status |
|---|---|---|
| All Patients | | All           |

| Status ▲ | | Bed and Ward | Patient Name |
|---|---|---|---|
| | SEPTIC SHOCK<br>17 Apr, 09:10, 0 Days | ITS BOX 2<br>11c | Test_Patient_03, Ludwig<br>male, 51 years, 117 kg, Day 1 |
| | SEVERE SEPSIS<br>17 Apr, 08:21, 0 Days | ITS BOX 4<br>Other | Test_Patient_06, Peter<br>male, 73 years, 67 kg, Day 1 |
| | SEVERE SEPSIS<br>17 Apr, 08:20, 0 Days | ITS BOX 5A<br>Other | Test_Patient_13, Günni<br>male, 27 years, 74 kg, Day 1 |
| | SEPSIS<br>17 Apr, 08:21, 0 Days | ITS BOX 3B<br>Other | Test_Patient_05, Susanne<br>female, 58 years, 61 kg, Day 1 |
| | SIRS and Organ Dysfunction<br>17 Apr, 08:20, 0 Days | ITS BOX 5B<br>Other | Test_Patient_14, Dörte<br>female, 57 years, 55 kg, Day 1 |
| ○ | SIRS<br>17 Apr, 08:45, 0 Days | ITS BOX 8<br>11b | Test_Patient_09, Bernd<br>male, 57 years, 92 kg, Day 1 |
| ○ | No SIRS<br>17 Apr, 08:20, 0 Days | ITS BOX 7B<br>11a | Test_Patient_08, Gundis<br>female, 49 years, 69 kg, Day 1 |
| ○ | No SIRS<br>17 Apr, 08:21, 0 Days | ITS BOX 1B<br>11b | Test_Patient_02, Hilde<br>female, 41 years, 57 kg, Day 1 |
| ○ | No SIRS<br>17 Apr, 08:21, 0 Days | ITS BOX 3A<br>Other | Test_Patient_04, Ulli<br>male, 44 years, 78 kg, Day 1 |
| ○ | No SIRS<br>17 Apr, 08:21, 0 Days | ITS BOX 1A<br>11a | Test_Patient_01, Klaus<br>male, 35 years, 85 kg, Day 2 |
| ○ | No SIRS<br>17 Apr, 08:21, 0 Days | ITS BOX 7A<br>11d | Test_Patient_07, Paula<br>female, 25 years, 84 kg, Day 1 |
| ○ | No SIRS<br>17 Apr, 08:20, 0 Days | ITS BOX 9B<br>11d | Test_Patient_11, Ines<br>female, 56 years, 54 kg, Day 1 |

| First Page | | Previous Page | 1/2 |

Patient Count: 14

| Note | PF ratio | WBC 1/μl | CRP mg/l | PaCO2 mmHg | Confirmation | |
|---|---|---|---|---|---|---|
| 📝 | 500 | 8000 | 100 | 45 | ✓ Confirmed Dr. Mueller, 17 Apr, 09:10 | > |
| 📝 | 200 | 4100 | 200 | 41 | ✓ Confirmed müller, 16 Apr, 17:43 | > |
| 📝 | 200 | 4100 | 100 | 41 | ! Confirm! | > |
| 📝 | 300 | 3800 | 100 | 35 | ✓ Confirmed müller, 16 Apr, 17:48 | > |
|  | 200 | 4400 | 0 | 39 | ! Check infection | > |
|  | 500 | 8000 | 100 | 45 | ! Check infection | > |
|  | 500 | 8000 | 100 | 45 |  | > |
|  | 500 | 8000 | 100 | 45 |  | > |
|  | 500 | 8000 | 100 | 45 |  | > |
|  | 500 | 8000 | 100 | 45 |  | > |
|  | 500 | 8000 | 100 | 45 |  | > |
|  | 200 | 4100 | 100 | 41 |  | > |

Sort by: Status

Dr. Müller

Next Page | Last Page

Connected

Smart Guard Sepsis 1.0 - Patients Logbook

| Patients List | | SEPTIC SHOCK<br>17 Apr, 09:10, 0 Days | ITS Box 2<br>11c |

Logbook

▼ Sepsis Status Timeline

Status

⊠ SEPTIC SHOCK
◧ SEPSIS
▨ SIRS

08:23　08:33　08:43　08:53　09:03　t

| Time | Status | | Confirmation Status | |
|---|---|---|---|---|
| 17.04.2013 09:10 | ⬟ | SEPTIC SHOCK | ✓ | Confirmed, Dr. Mueller |
| 17.04.2013 09:08 | ⬟ | SEPTIC SHOCK | ! | Confirm! |
| 17.04.2013 09:03 | ⬢ | SEVERE SEPSIS | ✓ | Confirmed, Dr. Müller |
| 17.04.2013 09:02 | ⬢ | SEVERE SEPSIS | ! | Confirm! |
| 17.04.2013 09:01 | △ | SIRS and Organ Dysfunction | ! | Check infection |
| 17.04.2013 08:56 | ○ | SIRS | ! | Check infection |
| 17.04.2013 08:21 | ○ | No SIRS | | |

| First Page | | Previous Page | 1/1 | |

Patient Count: 14

Fig. 8B

| | Dr. Müller | ⚙ | ? |

Test_Patient_03, Ludwig  3321445744
männlich, 51 years, 117 kg  L.O.S. 1 Days    ✓ Confirmed Details Logbook

SEVERE SEPSIS

Trend Time Scale

1 Hour

SIRS and Organ Dysfunction

| Note | Critical Measurements | | | |
|---|---|---|---|---|
| Hip joint replacement | catecholamine within last 24 h | SC_BT °C 34,0 | SC_RR 1/min 23 | PLT 1/μl 85000 |
| Hip joint replacement | catecholamine within last 24 h | SC_BT °C 34,0 | SC_RR 1/min 23 | PLT 1/μl 85000 |
| Hip joint replacement | SC_BT °C 34,0 | SC_RR 1/min 23 | PLT 1/μl 85000 | |
| Hip joint replacement | SC_BT °C 34,0 | SC_RR 1/min 23 | PLT 1/μl 85000 | |
| | SC_BT °C 34,0 | SC_RR 1/min 23 | PLT 1/μl 85000 | |
| | SC_BT °C 34,0 | SC_RR 1/min 23 | | |

Next Page                                Last Page

Connected

Smart Sepsis Guard 1.0 - Ottmar Behrlage

| Patients List | ◯ SIRS <br> 16 MAR 2012, 10:23, 5 Minutes | ITS Box 1 B <br> Ward/Room |

🗐 Logbook

▼ Sepsis Status Timeline

Status — SIRS — timeline chart (00:00 – 06:00 – 12:00 – 18:00 – 00:00) — t

| Time | Status | Confirmation Status | Notes |
|---|---|---|---|
| 03 MAR 2012, 10:50 | ◯ No Infection | ✓ No Infection, Dr. House | 📋 |
| 03 MAR 2012, 10:55 | ◯ SIRS | ✓ No Infection, Dr. House | 📋 |
| 03 MAR 2012, 11:00 | ◯ SIRS | ✓ No Infection, Dr. House | 📋 |
| 03 MAR 2012, 11:05 | ◯ SIRS | ✓ Infection, Dr. House | 📋 |
| 03 MAR 2012, 11:10 | ◉ SEPSIS | ✓ Confirmed, Dr. Müller | 📋 |

| Jump to Start | ▲ |

Status Update: ▬▬▬▬▬▭▭ 1:30 Minutes ↻ Patient guarded since: 3 Days

| | 🔒 Dr. Müller | 👓 | ⚙ | ❓ | |

Test Patient 1  7824032648  📋  ❗ Check Infection
Male, 60 Years, *10 Oct 1952  L.o.S.: 5 Days SEPTIC SHOCK   ▨ SEVERE SEPSIS        Trends Time Scale
SEPSIS         ▨ SIRS + Organ Dysfunction   24 hrs (1 Day)
SIRS 🧍 Details 📖 Logbook

| BT(°C) | HR(bpm) | RR(bpm) | WBC(µ/l) | Immature Forms(%) | Glucose(mg/dl) | CRP(mg/l) | P |
|---|---|---|---|---|---|---|---|
| 36,7 | 90 | 70 | 2130 | 17 | 133 | 13 | |
| 38,3 | 95 | 75 | 2138 | 19 | 121 | 12 | |
| 38,0 | 113 | 77 | 2200 | 21 | 120 | 11 | |
| 39,0 | 113 | 85 | 2312 | 21 | 120 | 14 | |
| 39,2 | 113 | 90 | 2314 | 23 | 123 | 15 | |

▼                                                              Jump to End

🗄 Connected 10:53

B

MONITORING UNIT FOR THE ELECTRONIC MONITORING OF SENSOR SIGNALS WITHIN THE FRAMEWORK OF THE MONITORING OF SEPSIS AND A CORRESPONDING PROCESS

CROSS REFERENCE TO RELATED APPLICATIONS

This application claims the benefit of priority under 35 U.S.C. § 119 of German Patent Application DE 10 2014 002 172.6 filed Feb. 19, 2014, the entire contents of which are incorporated herein by reference.

FIELD OF THE INVENTION

The present invention lies in the fields of medical device technology and electronics and pertains especially to a device, a process and a computer program product for the electronic monitoring of sensor signals within the framework of a clinical monitoring of sepsis.

BACKGROUND OF THE INVENTION

Support means for diagnosing sepsis and the stages thereof require the detection and testing of a great variety of values and vital parameters (for example, hemodynamic values, respiration values, blood gas analysis values or other laboratory values or measured values of medical devices, for example, heart rate-measuring devices, etc.) at regular intervals. These measured values and sensor signals are typically acquired at different times and with different devices and are thus available in a distributed form (in the sense of information technology).

The following septic stages and statuses exist:
1. SIRS syndrome (Systemic Inflammatory Response Syndrome). This status is defined by at least two of the following criteria:
   Fever or hypothermia, confirmed by rectal, intravascular or intravesical measurement,
   Tachycardia with a heart rate above 90 beats per minute,
   Tachypnea with a rate of 20 beats per minute, or hyperventilation (arterial partial pressure of $CO_2$, $PaCO_2 < 4.3$ kPa $< 33$ mmHg)
   Leukocytosis (>1,200 per mm3) or leukopenia (<4,000 per mm3) or >10% immature neutrophils in the differential blood count,
2. Sepsis, defined as SIRS as a response to an inflammatory process,
3. Severe sepsis, defined as sepsis with organ dysfunction or with tissue hypoperfusion, and
4. Septic shock as severe sepsis as well as a systolic arterial blood pressure of <90 mmHg for at least 1 hour.

The diagnosis of sepsis or a septic status is a highly complex, multistep process, which is based on a large number of different sensor data. There are guidelines for the prevention, diagnosis, therapy and aftercare of sepsis (for example, by the Deutsche Sepsisgesellschaft e. V. [German Sepsis Society, registered association], hereinafter also called DSG, and an equivalent in the USA, the Surviving Sepsis Campaign, SSC).

Current studies show that sepsis develops, as a rule, slowly and with only small changes in the vital parameters (usually in a time window of 24 hours), which are at times very difficult to notice. The detection of a septic status therefore often remains unnoticed. The mortality rates associated with a septic status are alarmingly high: 30% to 50% mortality rates for severe sepsis and 50% to 60% for septic shock can be noted. If a septic status remains undetected and thus untreated, this consequently means a dramatic worsening of the patient's status. Conversely, the sooner therapeutic measures can be taken, the better are the chances for the affected patient.

Various systems are known in the state of the art in the device-based, preparatory support for diagnosing a septic status. Thus, especially the "Eventmanager" system MetaVision of the firm of imdSoft, and the "Clinical Advisories" system "IntelliVue" of the firm of Phillips are known. Both systems are also used to diagnose sepsis and are implemented in a patient data management system. The user can configure a rule engine in order to make possible the automatic detection of changes in the patient's status by means of the product. A tabular view ("flow sheet") is displayed with a curve showing the changes in the measured values over time. The user disadvantageously does not receive any information or any display of previous measured values and previous statuses (concerning the "Clinical Advisories" system).

Furthermore, it proved to be disadvantageous in practice that the user can obtain the necessary information only by clicks and a review of several views on the user interface. Furthermore, the normal range for the respective signals and parameters is not always outputted (graphically), which makes the operation of the system, on the whole, difficult, and may sometimes cause life-preserving measures to be initiated too late.

It is important for a user to obtain information on the sepsis-relevant data sets as rapidly and in as clear a form as possible. In addition, it should be visible in a short time and quasi at a glance where or in which patient there is a detailed need for action (for example, in the form of the acquiring further sensor data or in the form of the initiation of therapeutic measures).

It is also desirable to sort and/or filter according to the different degrees of severity of a sepsis (septic status) and according to the confirmation of a septic status that has yet to be made. Furthermore, the signal data or parameter values that are being monitored and/or are (still) missing shall be identified.

Another system known in the state of the art is the "Protocol Watch" system of the firm of Philips. This system also displays parameters that are important for the diagnosis of sepsis. The normal values or permissible values are likewise visualized with the current values during the visualization of this system. One drawback of this system can, however, be seen in the fact that the display of graphic curves describing the signals is limited only to 12 hours.

Furthermore, the selection of the displayed values is fixed and hence limited. Another considerable drawback can be seen in that the user does not obtain any information on the extent to which noncompliance with limit values of a parameter affects the assessment of sepsis and on the extent to which the exceeding of a limit possibly interacts with other parameter values. Since further measures are, as a rule, time-critical and rapid acquiring of sepsis-relevant data sets is indispensable, it is desirable to have a graphic display of the relevant data sets in an overview display.

SUMMARY OF THE INVENTION

Based on the above-described state of the art, a basic object of the present invention is to overcome the above-mentioned drawbacks of the prior-art systems, and to provide an improved system for the electronic monitoring of sensor signals within the framework of the monitoring of sepsis. Furthermore, a graphic display of the changes over time in sepsis-relevant sensor data or parameter values shall also be possible over a longer time period in an overview display. In addition, the display shall be dynamic and/or interactive in order to sort, filter, group and/or prioritize the data sets displayed. An important aspect can also be seen in the fact that rules applied in respect to sepsis are displayed comprehensibly insofar as the sensor data causing the sepsis are identified in the visualization.

In an overview display, the user shall obtain an overview of the septic statuses from all sensor signals of the patient which are being monitored at a glance. All patients affected by sepsis or with suspected sepsis shall be combined in the overview display. The overview display shall overlap all departments and also comprise a configured set of sepsis-relevant measured values and the instances in which the actual values are above or below the normal values for each patient, besides the automatically detected septic status of each patient. The overview display shall be interactive, so that the user can initiate further actions here.

In addition, a patient-specific detail view shall be generated, which displays in a graphic form all the sepsis-relevant signals, signal curves and parameter values in reference to permissible limit values and instances in which limit values are exceeded, as well as the respective current value. Furthermore, limit values not complied with shall be identified in a classified form and corresponding to a septic status caused by an instance in which the actual value is above (or below) the limit value.

Finally, a history or logbook view shall be provided, in which previous and past instances of assessments and status calculations are displayed with a curve. It shall also be possible to record notes on acquired sensor signals and/or infections or septic statuses confirmed by the user in order to make all status calculations and assessments comprehensible. A synchronized display of trends together with a tabular display of at least one detail of the results of the status calculation shall offer an efficient overview to the user.

An identification of instances, wherein limit values are exceeded after an acquisition of a request signal on a user surface, may comprise the outputting of information on the exceeding of limit values, which pertains to a time at which the limit value was exceeded and/or to the corresponding parameter value and/or the signal value.

An identifying of instances, wherein limit values were exceeded, may advantageously be performed in a status-specific manner.

The status calculation may be at least one of automatically calculating and displaying changes in status in an updated form at preconfigurable intervals.

The visualization of the results of the status calculation may automatically displays changes in status in an updated form at preconfigurable intervals.

The monitoring unit may be integrated in a mobile terminal telecommunication terminal.

The monitoring unit may further comprise at least one alarm signal transmitter for outputting at least one of an alarm signal and an interactive emergency signal receiver.

The present invention will be described below on the basis of the device. Embodiments, alternative solutions with further features and advantages mentioned here can also be applied to i.e., the process and the computer program and the computer program product and vice versa. Features described for the device, can also be applied to the process or a system and vice versa. The corresponding functional features of the process are implemented by corresponding circuit modules or microprocessor blocks, which are designed to assume the corresponding functionality. For example, a process step of "storage" may be implemented by a memory or as a data bank access, which is designed (configured) to store the data set in question.

The present invention pertains to a monitoring unit for the automatic monitoring of sensor signals or parameters within the framework of a medical monitoring of sepsis. The monitoring unit comprises:
- a monitor for visualizing results of a status calculation;
- a sensor data acquisition interface, which is intended to acquire status-relevant sensor signals of medical devices;
- a rule engine interface to a memory, in which rules for analyzing and/or processing status-relevant parameters and/or sensor signals are stored;
- a computer-assisted control unit, which comprises an arithmetic unit, wherein the arithmetic unit is supplied with sensor signals via the acquired sensor data acquisition interface; wherein the computer-assisted control unit is designed (configured) to dynamically control the visualization of the status calculation on the monitor with the use of the rules defined for the status calculation and stored in the memory such that:
  - the visualization comprises an overview display overlapping all patients, and/or
  - the visualization comprises a detail view structured in parameter tiles, wherein a display of the course of the sensor signal over time is visualized in each parameter tile of the detail view besides a currently measured sensor signal, and/or
  - the visualization of the results of the status calculation comprises a logbook view comprising a trend graph.

It should be expressly noted that the above-mentioned three embodiments may also be combined and that all three visualizations are preferably implemented.

The terms used within the framework of this patent application will be explained in more detail below.

The monitoring unit is a physical, objective device, which is preferably used in the field of clinical intensive care. It is provided with corresponding interfaces to be connected to other medical devices and/or patient data management systems. This electronic device comprises a monitor for visualizing results of a status calculation. In an alternative embodiment, the monitoring unit is integrated in another device. In another embodiment, the monitoring unit may be implemented as a hardware implementation (e.g., as ASIC (ASIC: Application Specific Integrated Circuit) or as FPGA (FPGA: Field Programmable Gate Array). In another, likewise preferred embodiment, the monitoring unit may also be implemented entirely or partly as a software application, which may be provided on different systems. It is thus possible, on the one hand, to provide the software-implemented sections of the monitoring unit on a stand-alone computer (personal computer, computer network, mobile terminal, laptop, etc.) or to integrate or implement it in a patient data management system. The monitoring unit may otherwise also be implemented as a physical structural unit in an electronic device. An especially preferred embodiment pertains to the implementation of the monitoring unit on a mobile terminal (e.g., tablet PC). The mobile terminal may comprise a touch screen (as a touch-sensitive display). One embodiment pertains to a surface-capacitive touch screen. Alternative embodiments pertain to inductive or projected capacitive touch screens.

The monitoring unit has input and output interfaces, e.g., mouse, touch screen and/or keyboard with cursor keys. The operation of the monitoring unit is access-protected, so that only authorized users can log in and make inputs. User-side inputs may be made via buttons providing a graphic surface (e.g., the sorting, filtering, storage, export, confirmation or changeover between the different pages of the visualization of the status calculation).

The sensor signals are analog or digital signals, which are acquired by different medical devices, comprising laboratory devices (for example, for blood analysis), body temperature-measuring devices, respiration rate-measuring devices, blood sugar-measuring devices, etc. The sensor signals are usually time-discrete signals (or parameter values) or time-continuous signals, which are measured continuously or at intervals on specific devices. It is also possible, as an alternative, to input the sensor signals via an averaging system, for example, a patient data management system, in which the different vital parameters are consolidated and collected, rather than directly from the acquisition devices. The sensor signals are used as input variables (inputs) for the status calculation. The term "sensor signal" shall be defined, in principle, broadly, and it also comprises, besides the corresponding measured values, other parameter values as well, which are stored, for example, in the patient data management system and are especially relevant for the monitoring of sepsis.

The preferred embodiment of the present invention pertains to the monitoring of sensor signals within the framework of the monitoring of sepsis. However, the monitoring unit/system may also be used for other applications in a flexible manner by means of a corresponding configuration.

The term "status calculation" pertains to an automatic and computer-implemented calculation of an overall status, which is relevant for the assessment of a sepsis. The status calculation is especially patient-related and preferably comprises all sepsis-relevant sensor signals, sensor data and/or parameter values, which are already available. The status calculation may be patient-specific (detail view, logbook view) or it may be a status calculation overlapping all patients (overview display). Furthermore, it is also possible to visualize the variables that are important for the status calculation but are not yet available (e.g., because they have not yet been determined or because there is no data connection at present with the corresponding medical device). This leads to the advantage that the user is referred directly to necessary measures (e.g., for data acquisition).

The status calculation yields a result (output), which is visualized on the monitor. The visualization of the results of the status calculation is preferably interactive, so that buttons, with which a user can initiate further measures and/or processes (especially the display of a patient-specific detail view), are provided on the surface. One important point can be seen in the fact that individual sepsis-relevant aspects can be visualized for a graphic visualization in the form of graphic symbols or in the form of graphic diagrams (e.g., over the course of time). This has the advantage that the user obtains an overview of the relevant information quickly and efficiently. In addition, a tabular display may be provided as well.

As was mentioned above, the sensor data acquisition interface is designed (configured) either as an interface to the different medical devices (for acquiring the measured signals) or as an interface to a central system (e.g., to a patient data management system).

The rule engine interface is preferably an interface to a memory. The memory may be preferably designed as a data bank DB, in which the rules being stored and kept ready can be dynamically configured and in which a workflow is stored for processing the acquired sensor signals (measured values or parameter values). Furthermore, rules for analysis and processing are stored in the data bank. The data bank may be implemented as a knowledge base. Guidelines for assessing the sepsis may be stored in the knowledge base. The data bank and/or the knowledge base may be advantageously updated (for example, in order to be able to be adapted to new developments in sepsis research) independently from the monitoring unit and especially from the control unit of the monitoring unit.

The data bank is preferably connected to the monitoring unit as a separate instance. A rule engine may also be implemented in the data bank in order to specify how the particular sensor data or sensor signals and signal curves are to be processed.

The monitoring unit comprises a control unit. The control unit is an electronic component and may be implemented entirely or partly in hardware or software. The control unit (controller) is used to dynamically control the (preferably interactive) visualization on the touch screen. "Dynamic" means in this connection that the display in question is updated time and time again. Consequently, as soon as, for example, new sensor signals are available, the corresponding visualization on the monitor is updated. Corresponding control signals are likewise generated in case of corresponding user inputs, which are acquired on interactive buttons on the monitor or via another user interface, in order to achieve updating of the display. The control unit may be integrated in a graphic user interface or part of another graphic module.

In the preferred embodiment, the control unit also comprises an arithmetic unit, which is operated with the acquired sensor signals via the sensor data acquisition interface. In an alternative embodiment, the arithmetic unit may also be provided as a separate module in the monitoring unit or connected to the monitoring unit as an external module. The arithmetic unit is not part of the control unit in this case. The arithmetic unit is used, furthermore, for the status calculation. The rules stored in the data bank or in the knowledge base are used for the status calculation. The visualization comprises, besides an especially interactive (preferably tabularly structured) overview, a patient detail view, which is patient-specific and is structured in tiles. Each tile pertains here preferably to a sepsis-relevant parameter value. A parameter tile is a graphic display in a user surface section (window or window section) and comprises:

The display of the current measured value (e.g., body temperature, blood pressure, CRP value, etc.), a graphic display of the signal curve over time, wherein the time window can be preferably configured with the respective signal or parameter values while inserting (lower and/or upper) limit values.

According to one aspect of the present invention, at least part of the results of the status calculation is visualized in the parameter tile. Moreover, the tile also contains the identifying of the values of the respective signal (or parameter) that are not in the normal range and represent a sepsis-relevant exceeding (or undershooting) the limit value in a sepsis-relevant manner. A special aspect of the visualization of the parameter tiles can be seen in that noncompliance with normal values or normal ranges (i.e., exceeding/undershooting of a limit value) is identified directly in the graphic display (e.g., highlighted in color or by a different signal curve: Blinking or by a line pattern, e.g., dotted line). This also happens when the exceeding of the time limit (the term shall hereinafter also be used in the sense of an undershooting of the limit value) took place in the past and the current value is within the normal range. The user thus obtains information at a glance that there was an incidence in which a current value exceeded a limit value in a past time period and is informed of this.

Provisions are made in an advantageous variant of the present invention for the parameter tile to be interactive, so that the user can click on the respective signal value, for example, in case of noncompliance with normal values in order to obtain a detail view. For example, another time axis, which has a finer resolution, can be selected in the detail view generated in order to inform the user on when exactly the limit value was exceeded.

All the signals and parameters are visualized clearly in a window in the patient detail view. The user can thus obtain at a glance all the parameters that are relevant for the sepsis. The respective parameters are sorted into groups. The configuration of the patient detail view page can, however, be so as to make possible an efficient interpretation of the respective measured values. The curve of the respective signal or parameter over time is represented in the parameter tile view, as a rule, over time, which is also taken into account for the rule analysis, as a graphic trend, usually over the last 24 hours. The user can thus deduce directly how the parameter in question changed over time and recognize a trend. Special deviations from normal values may correlate with organ dysfunctions. If an organ dysfunction is present, the user is alerted by a corresponding signal on the user surface next to the corresponding measured value, which causes or is one of the causes of the organ dysfunction.

According to another embodiment of the present invention, the visualization comprises a graphic display of a classification of the sensor signals in sepsis classes according to the sepsis guidelines being stored in the data bank. Further classes in reference to the sepsis may also be added here in a phase of configuration. It is thus possible, for example, to also include a class for an unremarkable signal curve (no suspicion of sepsis) besides the above-mentioned four classes. Different symbols and/or different identifications are preferably assigned to the different sepsis classes. For example, a septic shock may thus be identified with red color and an angular symbol, while a sepsis is presented in yellow color (with a rounded symbol). This has the advantage that a user obtains even more information and can see at a glance which sepsis classification and hence which septic status was calculated. The instances in which limit values are exceeded in the corresponding sensor signals are preferably identified corresponding to the respective sepsis classification. Consequently, if, for example, the exceeding of the "heart rate" signal value is the cause of the "severe sepsis" classification, the causative signal value is displayed, for example, in the same color with another, corresponding highlighting as the "severe sepsis" sepsis class. Consequently, different identifications are used for different septic statuses. Different identifications are likewise used for the different instances in which limit values of the sensor signals are exceeded or undershot.

According to a preferred embodiment of the present invention, the visualization of the results of the status calculation comprises a classification with respect to the different stages of sepsis, which are mentioned in the introduction to the description of this invention (SIRS, sepsis at different stages, severe sepsis, etc.). The classification is represented and identified by a corresponding classification symbol, depending on whether a SIRS, a sepsis, a severe sepsis or a septic shock can be inferred from the data and signals acquired. The status calculation is not consequently a diagnosis, because it involves only a calculation and analysis of signals, which suggest a medical assumption or a suspicion. This suspicion will then have yet to be confirmed by a physician (the "Confirmation" button is used for this). The classification thus has preferably four steps and can nevertheless be expanded or modified as desired. It can be defined in the rules that certain sensor signals or the exceeding of limit values of such sensor signals bring about a change in status in respect to a sepsis classification (so that, e.g., the "sepsis" status is changed to the exacerbated "severe sepsis" status). The respective sensor signal data, which bring about a change in the status, would correspond in this case to the identification of the status that is displayed on the user surface. If, for example, a septic shock is identified by the color "orange" in an embodiment variant, all sensor signals that exceed a limit value and bring about the change in the status, which are consequently the cause of the classification of a septic shock, would automatically likewise be identified in orange. This automatic correspondence of the interacting data (causative sensor signals are classified in agreement or correspondingly as the status calculation brought about thereby) offers important advantages in terms of time and performance in the practical application. The user sees immediately which sensor signals have been used for which status class. "Status class" means in this connection the classification of the calculated status in the preconfigurable stages, e.g., SIRS, sepsis, severe sepsis. It should be noted in this connection that these statuses are not patient statuses but statuses of measured values, to which a status that represents a possible assessment is assigned simply by calculation. This possible assessment will always have yet to be assessed and confirmed in a subsequent step.

The visualization also shows whether the calculated status (classified to at least one of the above-mentioned four classes: SIRS, sepsis, . . . or also as "no infection") was already confirmed by the user and if so, more information can be obtained on the confirmation by means of an interactive button on the user surface (time: When was a confirmation signal acquired; identification of the confirming user, and possibly further user-defined data). In a preferred embodiment of the present invention, the confirmation status is displayed by a graphic symbol (e.g., as a checkmark), which is embedded in the corresponding sepsis classification symbol (e.g., heptagonal symbol highlighted in color). It can, of course, also be actuated that there is no information; a circular symbol identified in green with an integrated checkmark is visualized in this case. If, for example, no signal values can be entered at all, an "undefined" status can be defined as well.

According to another, advantageous embodiment of the present invention, instances in which limit values are exceeded (or undershot) are identified interactively. It thus becomes possible to acquire on the user surface a request signal, which brings about the output or visualization of information on instances in which limit values are exceeded. The information on instances in which limit values are exceeded contains more detailed information for the particular instance in which the particular measured signal exceeds a limit value. This information preferably comprises the respective concrete parameter value or signal value, the time and possibly also the duration over which the limit value was exceeded, and possibly even further data (this can be configured in a preparatory phase), so that, of desired, even more information on instances in which limit values are exceeded can be added.

The visualization preferably comprises an overview display in a tabular structure. The overview display is a patient-overlapping representation and consolidates all status calculations in a single, common screen display. The user can thus have an overview of all sepsis-relevant data sets of the entire hospital and/or of the entire department or over several amalgamations of hospitals. The overview display is especially a display overlapping the ward. The overview display likewise contains a representation of the particular class of sepsis calculated or proposed or confirmed (this is preferably performed according to the guidelines implemented in the data bank). The overview display contains a plurality of attributes per patient, which are visualized in one line. The attributes comprise an identification of the patient (e.g., by name or an identification number), a classification of the status (septic status), a position signal (e.g., by identifying the corresponding bed or department) and at least four configurable status-relevant parameters. In addition, another confirmation field may be provided as well. It is identified in the confirmation whether the septic status generated by the system has already been confirmed or not (unconfirmed). The confirmation may likewise be performed via a user interface by the medical staff entering a signal. In a preferred variant of the present invention, filtering and/or sorting can be performed in the overview display according to confirmed cases of sepsis and/or unconfirmed cases.

The visualization is outputted in the form of an overview display, a detail view and/or a logbook view. The above-mentioned visualizations will be described in more detail in the detailed description of the figures with reference to the figures.

According to another aspect, the present invention pertains to a process for the automatic monitoring of sensor signals within the framework of the monitoring of sepsis.

In addition, further actuating variables, properties, aspects and/or commands can also be derived from the status calculation in connection with the control of additional devices or components (for example, as to the values with which a respirator shall be actuated, etc.).

Consequently, not executing the above-mentioned steps of the process necessarily in the above-described order is likewise within the scope of the present invention. As an alternative, it is also possible, for example, to determine at first a status and then to generate a visualization with the different views. In another embodiment, the process steps may be interleaved with one another at least partially, so that at least one result of the status calculation is already visualized during the acquisition.

Moreover, it is possible that individual segments of the above-described process can be designed as individual commercial units and remaining segments of the process as other commercial units. The process according to the present invention can thus be executed as a distributed system, on different computer-based instances (e.g., client server instances). It is thus possible, for example, that the control unit itself comprises different submodules, which are implemented partly on a central system (e.g., a patient data management system) and partly on a browser of a mobile touch pad device and/or partly on other computer-based instances.

A further solution to the above problem pertains to a computer program product according to the attached claim. Another solution to the problem provides for a computer program, which comprises computer instructions. The computer instructions are stored in a memory of a computer and comprise commands, which can be read by the computer and are intended for carrying out the above-described process when the commands are executed on the computer. The computer program may also be stored on a storage medium, or it may be downloaded from a server via a corresponding network.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 3A is an exemplary view of an overview page with results of a status calculation according to a preferred embodiment of the present invention;

FIG. 3B is a view of a continuation of the overview page of FIG. 3A;

FIG. 8A is an exemplary view of a logbook view according to a preferred embodiment of the present invention;

FIG. 8B is a view of a continuation of the logbook view of FIG. 8A;

FIG. 9A is another, exemplary view of a logbook view according to a preferred alternative embodiment of the present invention;

FIG. 9B is a view of a continuation of the logbook view of FIG. 9A; and

DESCRIPTION OF THE PREFERRED EMBODIMENTS

The present invention will be explained below in more detail with reference to the figures with a number of exemplary embodiments.

Figure 1:
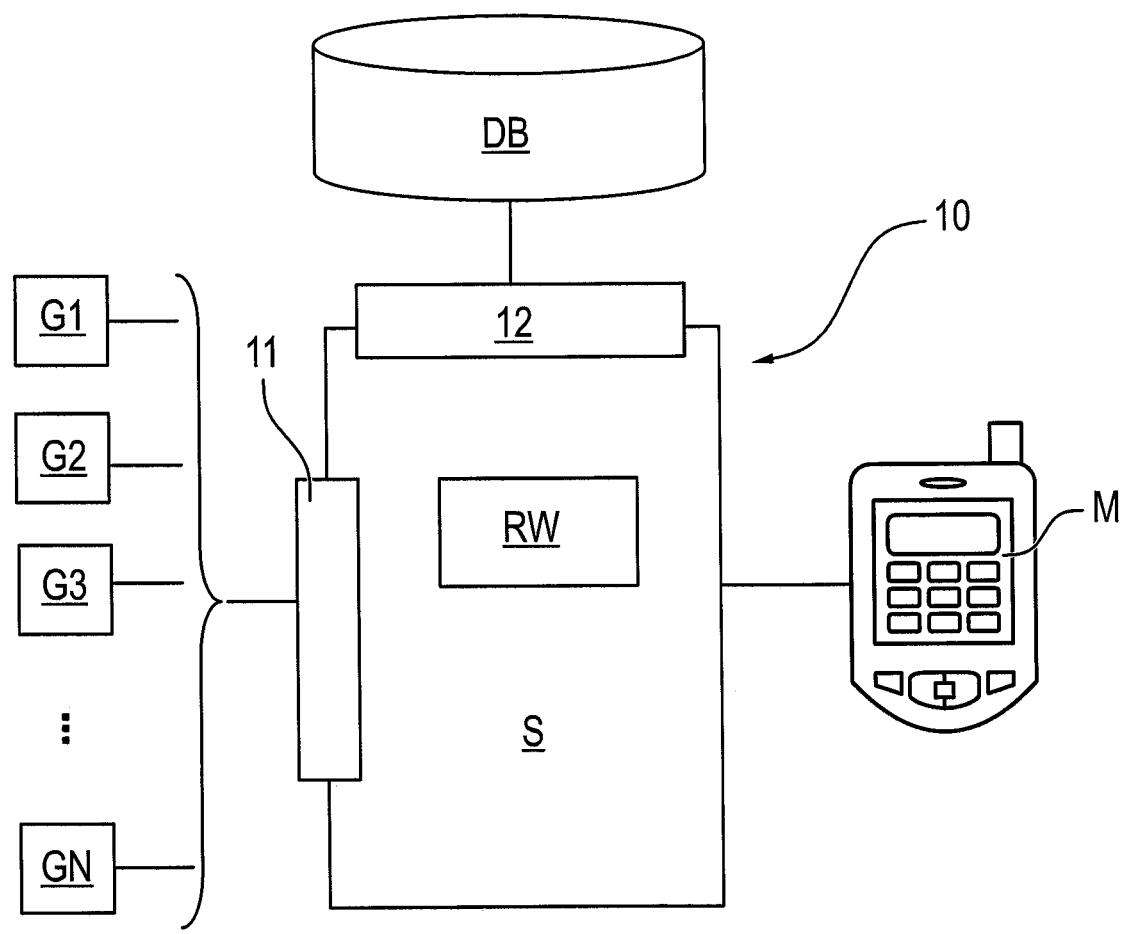
FIG. 1 is an overview and schematic view of a monitoring unit with functional units and interfaces according to a preferred embodiment of the present invention.

FIG. 1 shows basic functional units and blocks of a monitoring unit 10 according to a preferred embodiment of the present invention.

Figure 2:
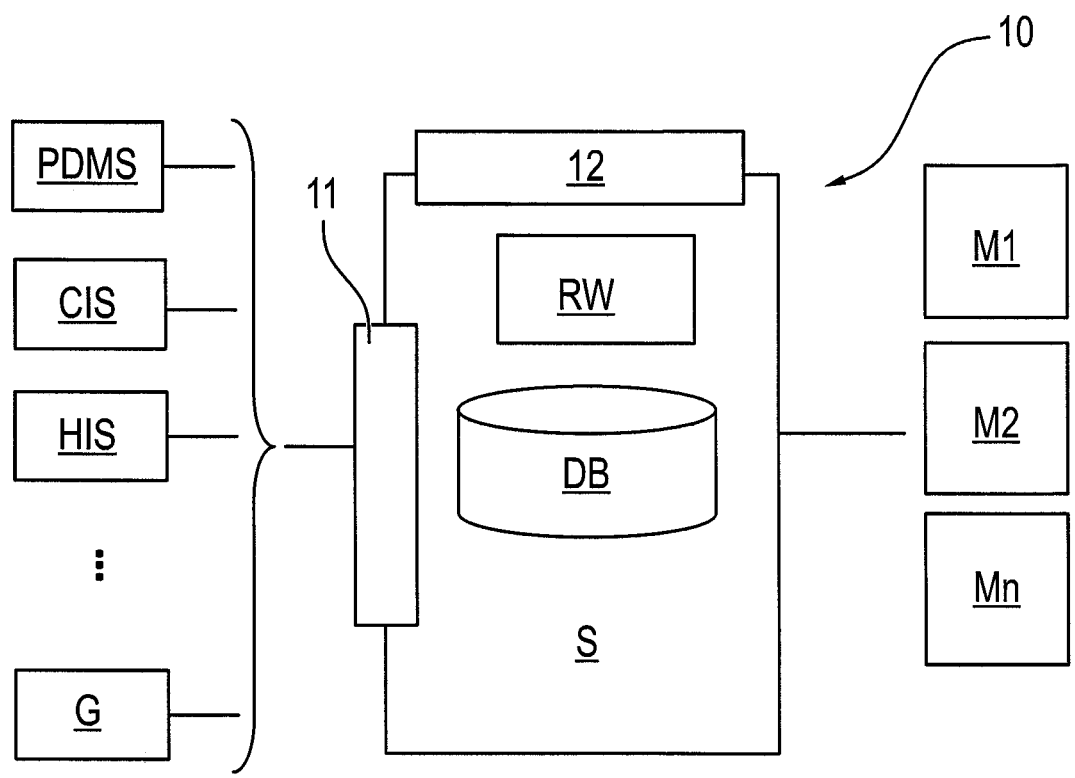
FIG. 2 is a schematic view of a monitoring unit according to an alternative embodiment of the present invention.

The monitoring unit 10 is in data exchange with a plurality of medical devices G, which are designated by the reference numbers G, G1, G2, G3 . . . Gn in the figures. The medical devices G are usually different devices, for example, body temperature-measuring devices, blood pressure-measuring devices, respiration rate-measuring device sand/or additional devices providing measured values. In addition, it is, of course, also possible to provide a plurality of measuring devices of the same type. The sensor signals acquired on the respective medical devices G are sent to the monitoring unit 10 via a sensor data acquisition interface 11. Furthermore, the monitoring unit 10 interacts with a data bank DB via a rule engine interface 12. The data bank DB in the embodiment shown in FIG. 1 is connected as an external instance to the monitoring unit 10. An alternative embodiment is shown in FIG. 2, and it will be explained in more detail below. The monitoring unit 10 comprises a control unit S and an arithmetic unit RW. The control unit S is used to dynamically control a status calculation on the monitor M. The status calculation is preferably interactive, so that a user finds buttons on the user surface to start actions. As soon as status-relevant changes arise in the data sets or in the acquired sensor signals, the status calculation is updated. This is what the term "dynamic" pertains to. The arithmetic unit RW is supplied with the acquired sensor signals and/or parameter values via the sensor data acquisition interface 11. Rules for the status calculation are stored in a memory block (with permanently coded rules) or in the data bank DB. To increase the flexibility of the system, a data bank DB is used, in which the rules stored in it can be dynamically configured (so that, for example, most recent research results of sepsis research can also be included). Furthermore, flow charts are also stored in the data bank DB for assessing sensor signals within the framework of the monitoring of a sepsis. The flow charts may be in the form of a computer-implemented (electronic) representation of guidelines. The guidelines may be issued by various institutes (e.g., the Deutsche Gesellschaft für Sepsisforschung [Germany Society for Sepsis Research] or sepsis research institutes in the USA). It can advantageously be achieved due to the separate storage of the rules for the analysis and processing of status-relevant sensor signals (and/or parameters) that the current research results can always be taken into account in the monitoring by the monitoring unit 10.

The visualization comprises at least one graphic display of sepsis-relevant values.

According to one aspect, the visualization comprises an overview display and/or a detail view. At least the detail view shows a display of the course of all status-relevant sensor signals over time for a patient. The detail view is preferably patient-specific and will be explained in more detail below.

An alternative architecture will be explained in more detail below with reference to FIG. 2. Contrary to the embodiment shown in FIG. 1, the sensor signals are not acquired here directly from the respective medical devices G, but from central systems, for example, a patient data management system PDMS, a clinical information system CIS, a hospital information system HIS and/or additional devices G. In addition, the data bank as a knowledge base is directly integrated in the monitoring unit 10. The monitoring unit 10 thus comprises the arithmetic unit RW in the control unit S and the knowledge base in the form of the data bank DB. The result, namely, the status calculation, is sent via a corresponding interface (which is not designated more specifically in the figures) to one or more monitors M. The monitors M may be, for example, part of a mobile terminal and designed, e.g., as a touch screen of a tablet PC. It is also possible, in principle, to display the status calculation on a plurality of monitors M1, M2, Mn. This makes sense, for example, when the sepsis monitoring is to be sent simultaneously to a plurality of users (e.g., attending physicians) of a hospital, who are responsible for a certain area.

It should be expressly noted that it is also possible to combine the system architecture shown in FIG. 1 with that shown in FIG. 2.

Thus, just as it is possible to place the data bank DB or the memory at an outside location (as is shown in FIG. 1), it is also possible to transfer the rule analysis to an outside location. Provisions may be made for this for the arithmetic unit RW to be connected as a separate instance to the controller or to the control unit S via a network (LAN or WLAN or other wireless or wired networks), the arithmetic unit RW being charged to assume the rule analysis function. A total of five separate modules are now provided in this case: The control unit S, which acts as a central controller, the data bank DB or the memory, the arithmetic unit RW, a patient data management system and/or a plurality of devices G as well as at least one client with an output unit, especially a monitor M. All instances interact via a network.

The sepsis monitoring system according to the present invention is preferably a web-based software application, which is activated both integrated in the patient data management system PDMS and remotely in a web browser (e.g., IE8, IE9, FF). As was mentioned above, the system can receive the sensor signals and parameter values to be monitored, e.g., via a suitable interface to the patient data management system PDMS. The interface is implemented by means of a JSON protocol. It is thus possible to bring about a bidirectional data exchange: On the one hand, the monitoring unit 10 receives the needed measured values via the interface to the PDMS, and, on the other hand, the PDMS persistently stores in its data bank DB, for a certain patient, all calculations and decisions in reference to the sepsis monitoring, which the monitoring unit 10 sends back via the interface.

FIGS. 3A and 3B show a patient overview display (also called simply overview display), which is structured as a table in the preferred embodiment, and has a patient-overlapping design. The overview display comprises all sepsis-relevant data sets for all patients of a configured section of the hospital (e.g., of the entire hospital, of an amalgamation of hospitals or of a department in the hospital). It shall thus be possible to obtain an overview of all patients and the related sensor signal data in order to diagnose sepsis as early as possible.

The patient overview display lists all sepsis-relevant data sets in a table for all patients. The overview display is access-protected and can be viewed by an authenticated user only in order to gain an overview of the septic statuses and to make it possible to recognize critical changes in the septic status in a ward-overlapping manner. The table (see FIGS. 3A and 3B) comprises a novel combination of the following columns in a preferred embodiment of the present invention:

Status of sepsis, date and time of diagnosis of this status, duration of time spent in the diagnosed septic status, Bed and ward as position data, Patient's name and/or patient identification, gender, age, body weight, during the hospital stay, Indicator for the reason of infection (patient-specific note)—This column visualizes whether the physician has filed a note for a certain patient in reference to an infection, Four configurable parameters with their units (the four configurable parameters may be selected and determined in a configuration phase. They are usually selected from the existing set of parameters for the diagnosis of sepsis according to the implemented guidelines.)

Confirmation, which the user can document concerning a septic status or infection (identified by the "confirmation" button in FIGS. 3A and 3B). This view is used basically to represent the need for action and expedites or improves the diagnosis process by prompting/guiding the user.

In a preferred embodiment of the present invention, the patient table comprises 7 columns (bed and ward, patient's name, note and the four parameter columns), which can be sorted in an alphabetically ascending and descending order when clicking on the corresponding column header, as well as two columns, which can be sorted according to defined semantics and logic.

The "Status" column can be sorted in an ascending and descending order according to the degree of severity of the diagnosed septic status in order to highlight the urgency of the patient's status. The prioritization and correspondingly the descending sorting order is as follows: Septic shock, severe sepsis, sepsis, SIRS and organ dysfunction, SIRS, no SIRS, undefined, suspended (see FIGS. 3A and 3B).

The "Confirmation" (confirmation) column is sorted according to pending user activity concerning the sepsis or infection, so that the physician can recognize right away in which patient a decision has yet to be made with respect to the confirmation of sepsis or infection. In addition, it is visualized in this column whether a confirmation has already been made for the particular patient and the following detailed information is also shown: The name of the physician who has made the confirmation and the corresponding date and time therefor.

The overview display additionally comprises a sorting button or a sorting function, which can also be used for sorting individual columns and brings about a link between clicking on the column header and clicking on the corresponding line in the popup from the sorting button.

Moreover, it is possible to provide a filter function. For example, the table can be filtered, clicking on the filter button, with still pending confirmations or infection tests. This is important because the confirmation or testing for infection must be performed as quickly as possible for the status in question for the benefit of the patient. This feature supports the medical staff in prioritizing its work with a large number of patients and communicates the urgency of a septic status, so that corresponding measures can be taken more quickly than before.

It is possible in an advantageous embodiment to filter according to the individual septic statuses (as stored in the data bank DB: SIRS, SIRS and organ dysfunction, sepsis, severe sepsis and septic shock) in order thus to arrive at a better overview and/or statistical analyses (e.g., on the course of the disease and its distribution among the patients in the entire hospital).

Since the system shows all configured wards to the user after a successful log-in, another feature, namely, the filtering according to individual wards, for which, e.g., the logged-in physician is responsible, is found to be very useful. The button shown in FIGS. 3A and 3B, which is identified in FIGS. 3A and 3B with "View" "All Patients," is used for this. A ward can be selected in the popup in order to focus only on the patients who are hospitalized in that ward and come into consideration for the logged-in physician.

The following statuses can additionally also be visualized in the status calculation:

1. Undefined if no data are (yet) available for the patient.
2. Suspended, if the connection with the patient data management system PDMS is interrupted.
3. Suspended, if the time from the system differs too greatly from the time from the patient data management system PDMS.
4. Suspended, if the patient is temporarily transferred.

If a patient is not being monitored with the early sepsis diagnosis system becomes visible in a short time by means of these statuses.

One important aspect can be seen in the fact that the automated analysis of measured values and/or decision support is displayed by the monitoring system in a comprehensible manner with a data bank symbol and a "Connected" keyword. It is ensured in this manner that the data displayed are up to date. In case of error (e.g., if the connection to the patient data management system PDMS or to the data bank DB fails), all patient entries are grayed out and the status of all patients changes automatically to "Suspended." In addition, the system status changes to "Disconnected" as well.

It is possible to combine the filter function and the sorting function. For example, certain user-defined combinations of filtering and sorting commands of critical septic statuses and pending user actions are found to be very helpful in the early diagnosis of sepsis and in connection with the degrees of severity or classification of the sepsis.

Provisions are made according to an advantageous variant of the present invention for displaying the four most important parameters in a table (see FIGS. 3A and 3B) corresponding to a status (e.g., patient status). The user is offered the possibility of deciding in the phase of configuration himself what these parameters shall be and the overview page can thus be individually adapted.

In one variant of the present invention, the overview page or overview display can be configured especially according to the user's wishes. The four parameter columns in the overview table (cf. FIGS. 3A and 3B) can be adapted individually by being configured by the user. The user may select from a parameter set predefined in the system. This represents a further support in the verification of the sepsis disease, because it becomes possible in this manner and by means of the visualization of the critical parameters for the physician to still treat the patient in time and to initiate measures in a specific manner.

Individual combinations of filtering (e.g., according to the status of the sepsis) and sorting of the table can be performed in another embodiment variant, which condenses the information and focuses and expedites the diagnosis of a certain septic status.

Figure 4A:
FIG. 4A is an exemplary view of a detail view with results of a status calculation according to a preferred embodiment of the present invention.
Figure 4B:
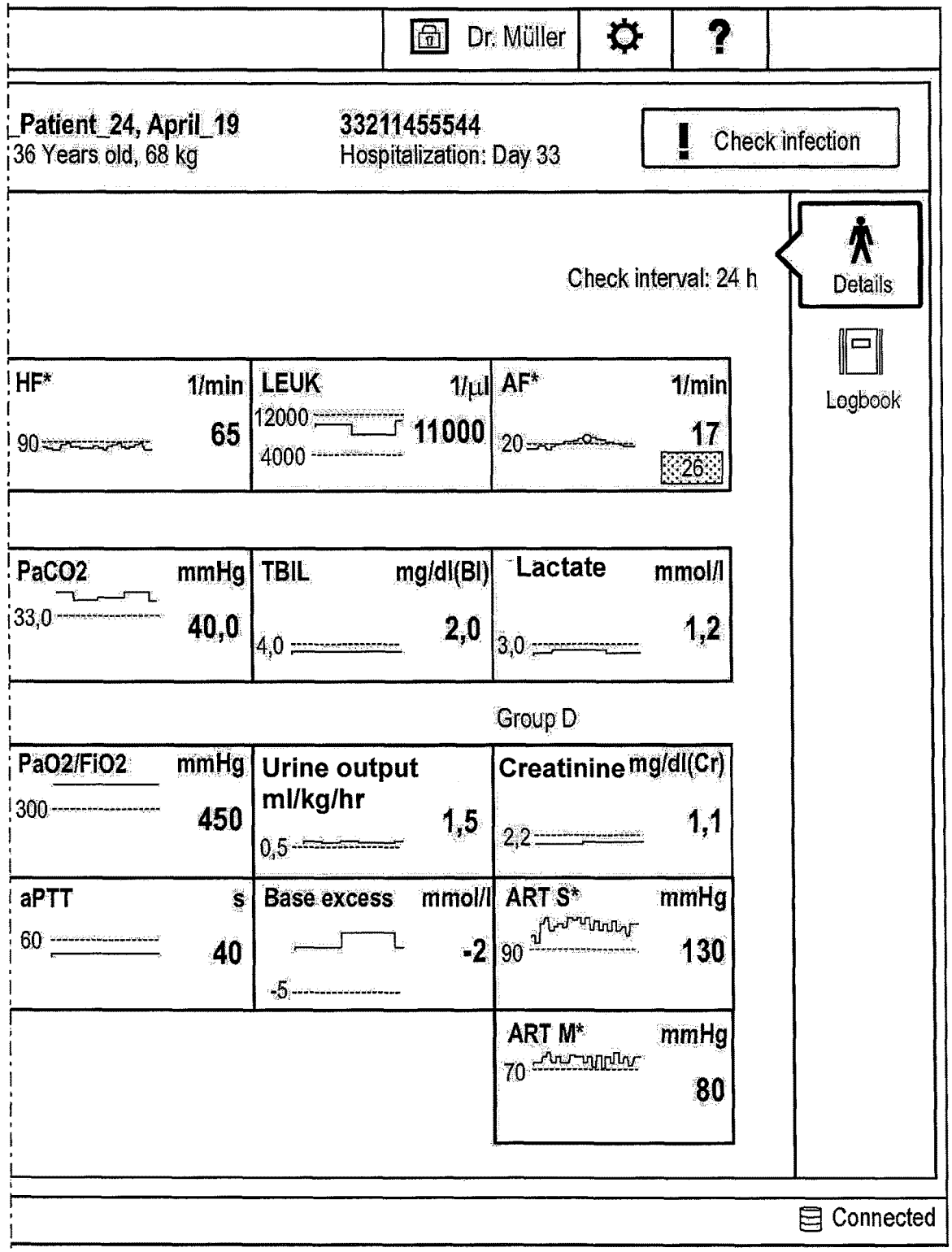
FIG. 4B is a view of a continuation of the results of the status calculation of FIG. 4A.

Based on an example, FIGS. 4A and 4B shows a detail view of the results of the status calculation. The detail view is structured in parameter tiles in order to display all relevant information for the user at a glance, in a rapidly detectable and condensed manner.

All the parameters that are relevant for an analysis within the framework of sepsis monitoring are shown in the detail view. The display is effected in groups, which can be configured by the user himself in the phase of configuration (which precedes the monitoring phase proper and is usually performed by an administrator at the time of putting into operation): Parameters may be added or removed and re-sorted in the order (the list of the parameters that are, in principle, available can be stored in the data bank DB). Relevant groups can thus be formed concerning certain issues in order to interpret measured values efficiently.

A block, in which various pieces of information are displayed, besides standard information, e.g., the name and unit of the parameter, is reserved for each parameter within a group.

Figure 5:
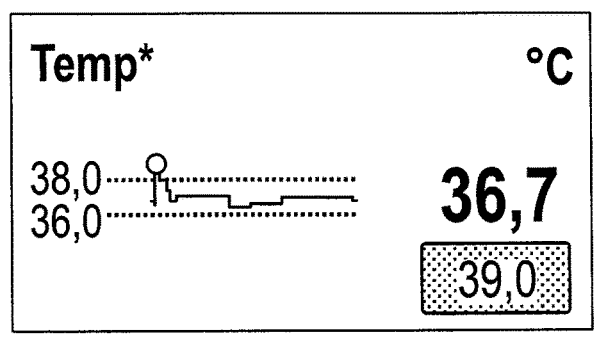
FIG. 5 is an exemplary view of information on instances in which limit values are exceeded in the form of a minitrend according to a preferred embodiment of the present invention.

Furthermore, information on instances in which limit values are exceeded may be displayed as needed, i.e., for example, when acquiring a user signal on the user surface. The information on instances in which limit values are exceeded may at times include the course of the corresponding parameter/sensor signal in question over time. This course is preferably displayed, as this is shown in FIG. 5 for an example, as a graphic minitrend over the time period that is also viewed for the diagnosis of sepsis (i.e., usually the last 24 hours). The concrete value of exceeding a limit value (39° C. at a limit value of 38.0° C.) is shown graphically highlighted, so that the user will immediately recognize the exceeding of the limit value at a glance and the time at which this occurred.

A graphic curve is plotted for the measured values determined, preferably in a non-highlighted format, e.g., in a neutral color (black). If the value or a plurality of values is/are beyond the normal range (i.e., if the limit value is exceeded, but the term shall be defined such that it also includes the case in which a current value is below a limit value), it is displayed as a dot or as a line in a clearly visible or highlighted manner, e.g., with a color. There exists a corresponding highlighting or color, which is used here, for each diagnosis (SIRS, SIRS+organ dysfunction, sepsis, severe sepsis, septic shock). This offers the advantage that the relevant data sets can be displayed for the user directly in a condensed form, without the user having to explore and sift through measured value tables. In addition, the limits for the normal range are identified in the trend, so that the fact that a value is (currently) outside this range or was also outside during the past period is communicated even more clearly. In its right-hand part next to the minitrend, FIG. 5 shows the most current measured value of the sensor signal or of the parameter as a numerical value (36.7° C.).

Figure 6:
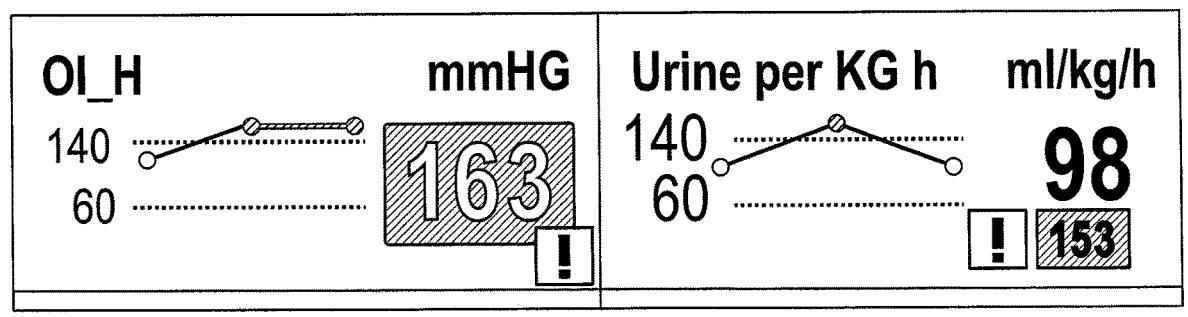
FIG. 6 is another, exemplary view of information on instances in which limit values of measured values are exceeded according to a preferred embodiment of the present invention.

If the measured value is outside the normal range (the limit value is exceeded) and the system has calculated on this basis a status, the measured value is highlighted in the corresponding color of the diagnosis. Should a previous value (e.g., one obtained 1 hour ago) rather than the current value be used in the status calculation, this value is shown below the current value, likewise highlighted correspondingly (in color). Which value is exactly included in the calculation of the diagnosis and possibly also how great the deviation is from the current measured value is thus clearly communicated to the user. This is shown in FIG. 6. A limited value was exceeded (value exceeding the limit value: 163 versus a limit value of 140) in both examples shown in FIG. 6; the limit value was exceeded currently in the first example shown on the left and at an earlier time in the past in the second example shown on the right (the current value is again within the permissible range).

Special deviations of values correlate with organ dysfunctions. If such a dysfunction is present, the user's attention is called to this fact by a separate symbol (see in FIG. 6: Attention—"!") in the corresponding display of the measured value. The "!" symbol, which represents an organ dysfunction on an output unit (monitor), shall be displayed in a prominent position on the user surface (window) of the display unit (especially under or above the current measured value in the trend/measured value graph, so that the user can recognize the risk associated therewith even more rapidly and clearly. The "!" symbol is also shown in the corresponding color of the associated status. If a user clicks on the attention symbol "!," the name of the organ dysfunction will be communicated to him. On the whole, severe pathological changes, which require quick action, will thus become transparent for the user.

If, for example a sepsis (or another status) develops and such a status is calculated, the user can see at a glance due to the highlighting in color (or in another manner) which parameters have left the normal range and when and are also included in the status calculation, even if these are values from the past considered for the analysis (usually the last 24 hours). The grouping of the parameters helps the user to combine the measured values, to relate them to one another and to analyze them according to special criteria (e.g., the curve showing the measured values over the last 24 hours). In turn, the user can comprehend on this basis the decision of the system rapidly and in a simple manner, validate it and take corresponding measures on this basis. To verify the sepsis, the user clicks on a button intended for that purpose (e.g., "! Check infection" in FIGS. 4A and 4B), changes the status correspondingly and thus confirms the current change in status of the system or of the monitoring unit 10.

Figure 7A:
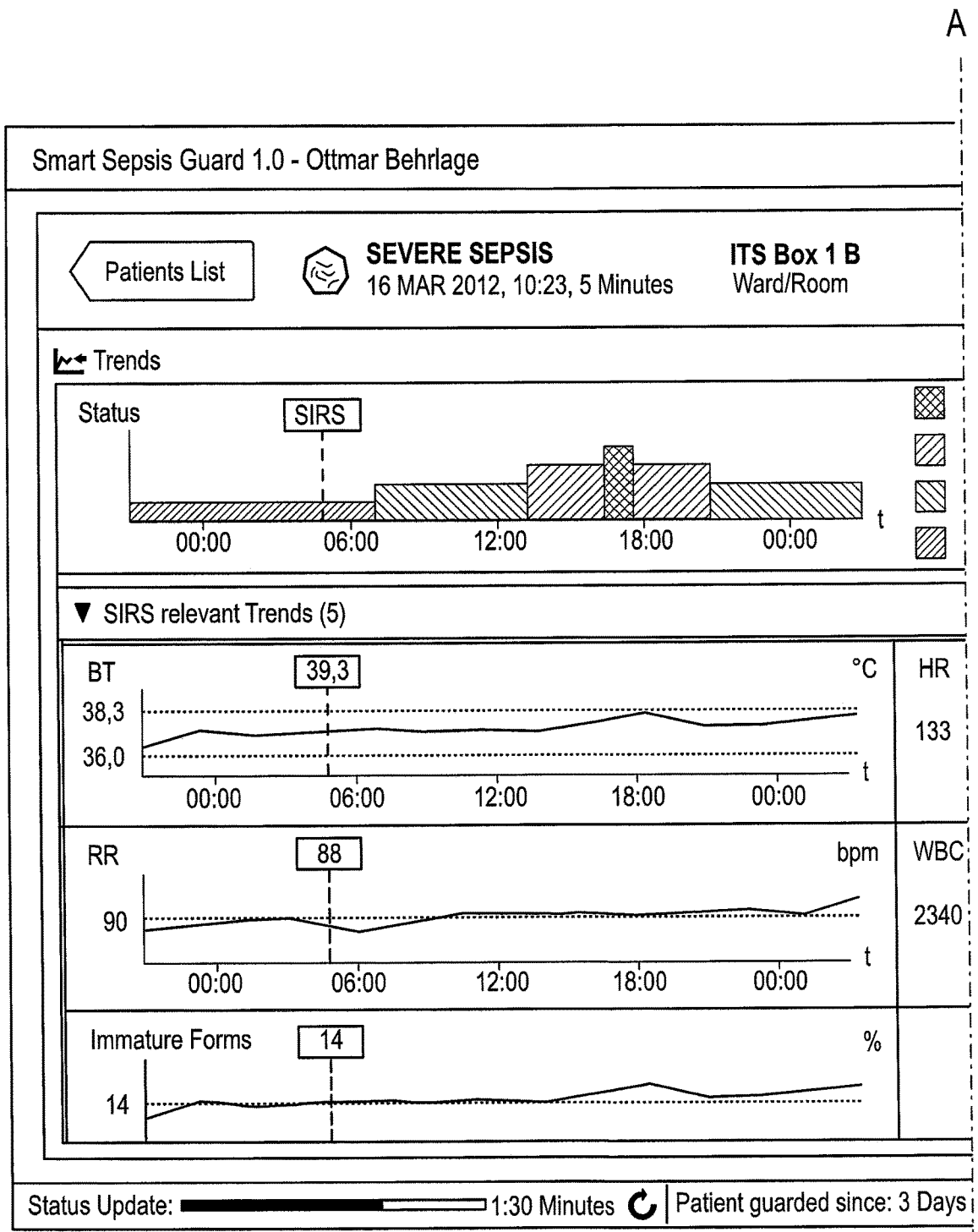
FIG. 7A is an exemplary view of trend details according to a preferred embodiment of the present invention.
Figure 7B:
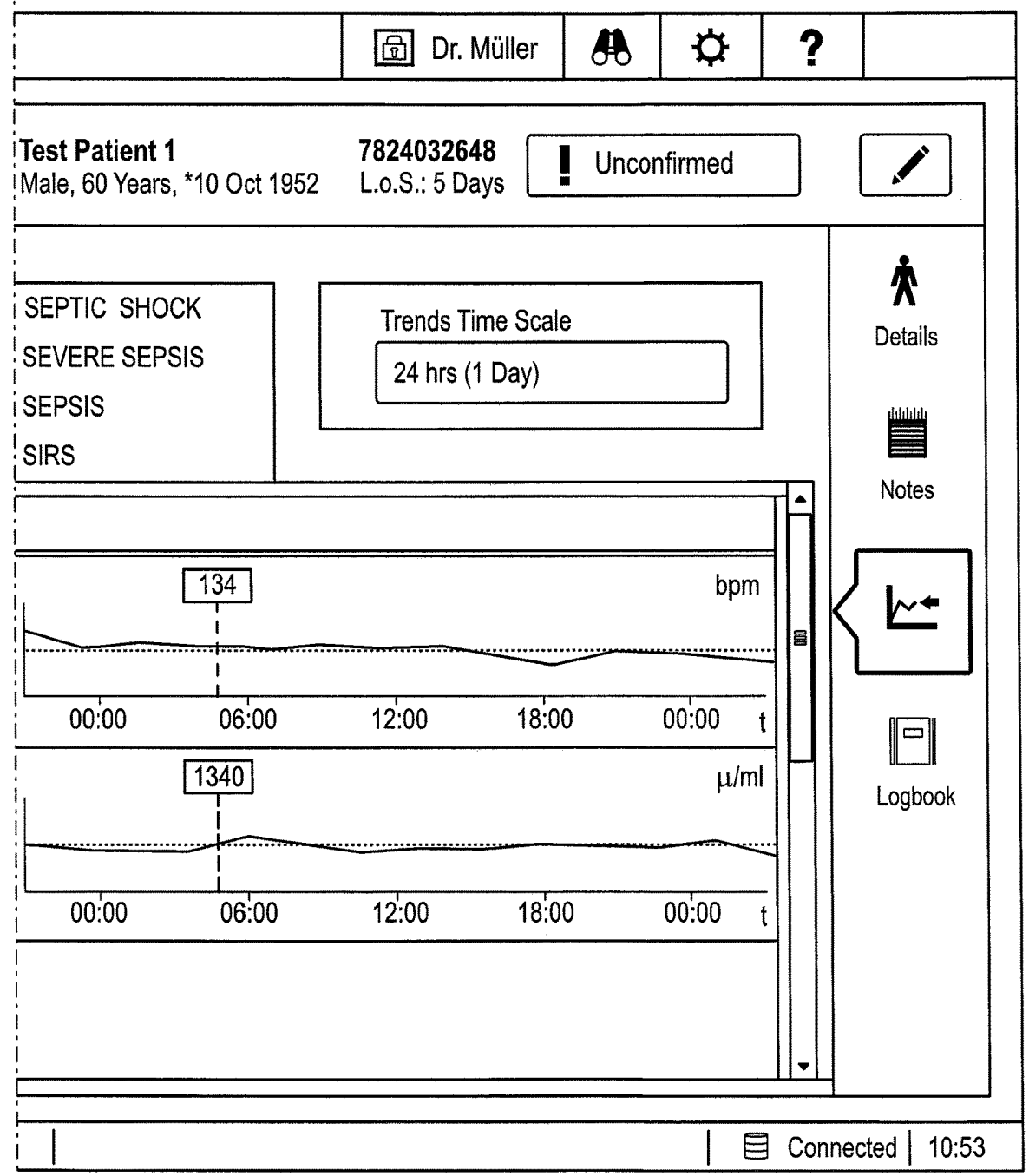
FIG. 7B is a view of a continuation of the trend details of FIG. 7A.

The minitrend functionality is expanded in an alternative embodiment of the present invention by a more detailed view of the history of a sensor signal or parameter as well as the possibility of interaction with the trend. This is shown in more detail in FIGS. 7A and 7B (especially in the lower section of the screen). The trend of a parameter is resolved more finely (especially in respect to the time axis) and thus it will have more details. In addition, an adjustable cursor helps in reading values directly from the trend (accurate reading is not possible in the minitrend graph, as shown in FIG. 5, but only an approximate estimate is possible). The trends of all parameters can be synchronized when adjusting the cursor, i.e., the same time will always be identified in the trend and the measured values belonging to this time can be displayed and examined more accurately.

In a preferred embodiment of the present invention, the status calculation comprises a page called "logbook." The logbook view of the monitoring unit 10 shows a graphic diagnosis trend and a measured value table concerning the history of measured values and diagnosis for a selected patient, as this is shown in an example in FIGS. 8A and 8B. The individual elements shall be described below.

Trend Graph:

The trend graphically shows the course of the different diagnoses (SIRS, SIRS+organ dysfunction, sepsis, severe sepsis, septic shock) detected by the monitoring unit 10 over time (selectable time period: 30 minutes, 1 hour, 2 hours, 4 hours, 8 hours, 12 hours, 24 hours, 7 days). A certain highlighting (e.g., in color) is assigned to each diagnosis. The diagnoses are plotted over time by means of bar charts, and a bar having a different height is assigned to each diagnosis ("the higher the worse"), which facilitates distinction. A legend helps identify the diagnosis corresponding to its color.

If the user selects an entry in the table located under it, the corresponding time is automatically identified in the diagnosis trend. The user this gains a good overview of the context of the entry. The diagnosis trend may also be closed if the user is interested in the table only.

Measured Value Table:

The table shows the time, status, confirmation status, note and critical parameters (which have led to the status) in a chronologically sorted form.

The table shows all the times (with the corresponding values) during the operation of the monitoring unit 10 at which sensor signals (or input parameters) were acquired and statuses were calculated. The table thus offers an overview of earlier diagnoses and the corresponding course.

The parameters that have run out of the normal range and thus contributed to making the corresponding diagnosis are displayed (exclusively) under the item "critical measurements." These parameters are stored, in turn, in color corresponding to the diagnosis in order to emphasize the septic status they cause. Depending on the number of parameters and the resolution of the display screen, it may, however, happen that not all parameters fit in the table and the user must scroll.

A corresponding note is displayed in the "Note" field, if available, for each entry in the table. This may provide information, e.g., on whether the data are valid or what further peculiarities, which are not detected in the application, were relevant at that moment.

Besides the decisions of the monitoring unit 10 ("status"), the table also shows detailed measured values of the patient. The user can thus thoroughly comprehend the behavior of the system.

It becomes visible in the "Confirmation Status" column whether a user has confirmed a calculated status or not. This retroactively provides the user information, on viewing the table, among other things, on how valid the diagnosis was.

The control components in the table make possible a quick and accurate navigation to certain elements within the table.

An advantageous variant of the present invention is shown in FIGS. 9A and 9B and pertains to the display of all parameters for the calculation of the diagnosis in the right-hand column (contrary to only those that have run out of the normal range). The advantage of this variant is that the values can be compared with one another more simply, because they are listed one under another in the table. However, the variant also makes it necessary for the user to perform an increased amount of horizontal scrolling in order to find the values—thus, the values are not usually on the common screen page.

Figure 10:
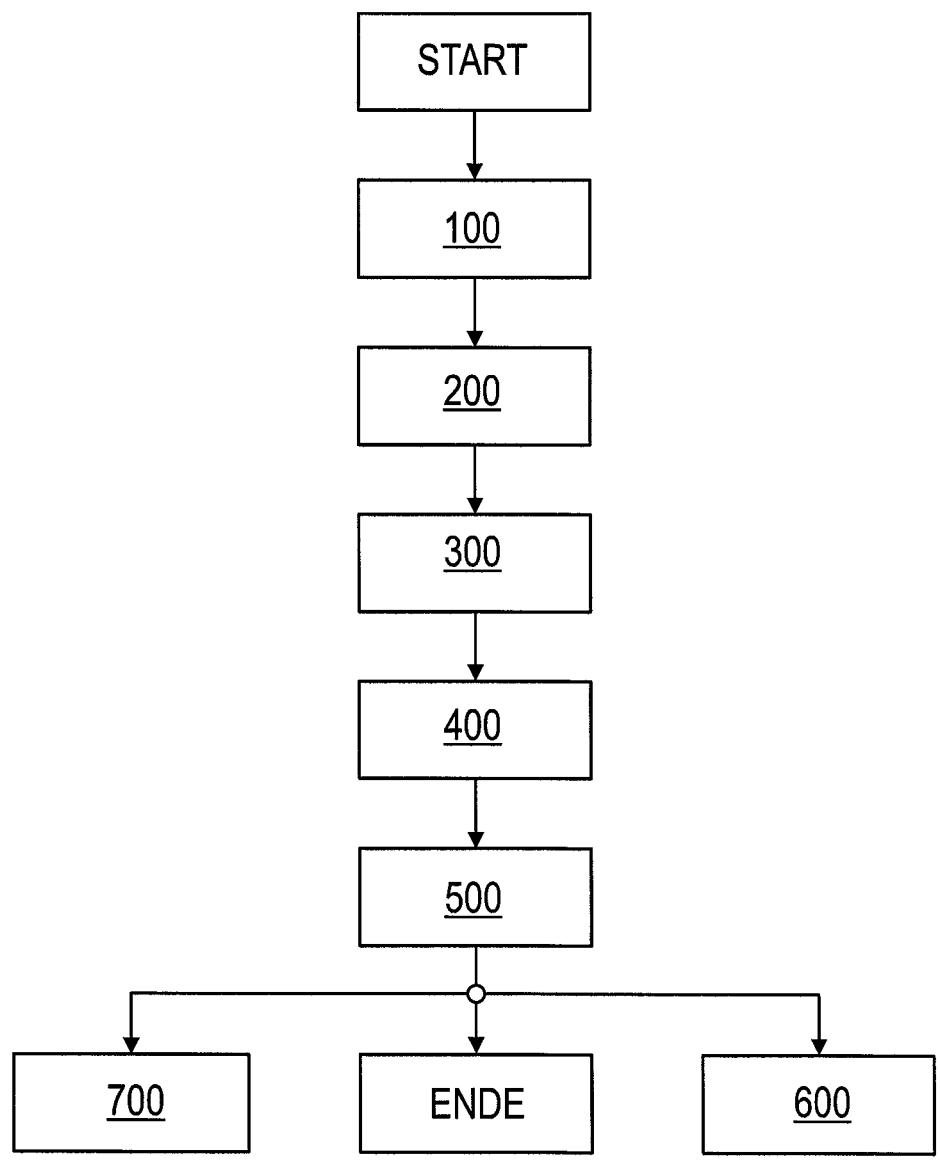
FIG. 10 is a flow chart for a monitoring process according to a preferred alternative embodiment of the present invention.

A possible workflow of a monitoring system or of a process, which can be carried out on the monitoring unit 10, will be described below with reference to FIG. 10.

Time-discrete sensor signals and/or parameter values are acquired in step 100 after the start of the system. The sensor signals are acquired by medical devices G and may also be stored in a patient data management system PDMS and entered from there.

The status calculation is performed in step 200. This takes place with access to the knowledge base DB with the rules stored there.

The calculated status is made available as a result of the status calculation in step 300.

The identification of all the sensor signals bringing about or causing the status is performed in step 400.

At least one of the above-mentioned outputs or visualizations, i.e., the overview display, detail view and/or logbook view, is generated in step 500.

Provisions are made in advantageous variants for generating an alarm signal in step 700 and outputting it to configurable receivers. Messaging may take place in step 600. This means that configured messages about information are outputted to likewise configurable receivers. For example, a message may be outputted here if a status has not yet been confirmed and is awaiting confirmation. The alarm signal is sent to receiver devices (e.g., pagers) via a communication connection (usually wireless data connection, e.g., radio or mobile telephone, etc.). A plurality of receiver devices may also be informed with the alarm signal simultaneously.

In its core, the present invention thus pertains to an automatic measured value monitoring or a monitoring of sensor signals on the basis of a configurable or permanently coded knowledge base in order to calculate an indication of a status for the monitoring of sepsis. The status is visualized in a detail view and/or a logbook view. The visualization is interactive and is based on symbols.

It should finally be noted that the above description of the present invention with the exemplary embodiments shall not, in principle, be understood to be limited in respect to a certain physical embodiment of the present invention. Thus, it is especially obvious to the person skilled in the art that the present invention is not limited, in principle, to the implementation of specific sepsis guidelines or certain types of monitors, but may also be used for other guidelines or monitors in stand-alone devices. Moreover, it is also not absolutely necessary to use the JSON protocol as an interface. It is thus also possible to use a communication technology based on an RPC and/or web service. For example, proprietary protocols may also be used for the process communication. Furthermore, the above listing of medical devices (blood pressure-measuring device, anesthesia apparatus, body temperature-measuring device, etc.) that are in data exchange shall not be considered to be a limiting listing and may also be expanded to other or additional devices. In addition, the present invention may be partly or fully implemented in software and/or in hardware. In addition, the monitoring unit or its control unit may also be embodied such that it is distributed among a plurality of physical products, comprising computer program products. It is thus possible to implement part of the monitoring and/or control on a terminal (e.g., a mobile terminal) and a remaining part on a server (e.g., one on which a patient data management system runs).

While specific embodiments of the invention have been shown and described in detail to illustrate the application of the principles of the invention, it will be understood that the invention may be embodied otherwise without departing from such principles.

What is claimed is:

1. A monitoring unit for the electronic monitoring of sensor signals related to sepsis monitoring, the monitoring unit comprising:
    a monitor for visualizing results of a status calculation of a septic status of a patient;
    a sensor data acquisition interface acquiring status-relevant sensor signals from medical devices, the status-relevant sensor signals comprising data associated with sepsis monitoring, the status calculation being based on the data associated with sepsis monitoring;
    a memory storing at least one of rules for analyzing status-relevant parameters and rules for processing status-relevant parameters and rules for sensor signals;
    a rule engine interface to the memory;
    a computer-assisted control unit comprises an arithmetic unit, wherein
    the arithmetic unit is supplied with the acquired sensor signals via the sensor data acquisition interface; and
    the computer-assisted control unit controls a visualization of the status calculation dynamically on the monitor based on the rules stored in the memory and intended for the status calculation such that the visualization comprises a detail view structured in parameter tiles; and each parameter tile of the detail view comprises a display of a visualized course of a sensor signal over time in addition to a currently measured sensor signal, wherein the parameter tiles comprise a column of parameter tiles, each of the parameter tiles in the column of parameter tiles comprising a display of the septic status and a degree of severity of the septic status of a respective patient, wherein the degree of severity is determined by comparing respective predefined limit values with currently acquired sensor signals, wherein the visualization of the results of the status calculation in the display comprises an identification of sensor signal values or parameter values that do not comply with limit values stored in the memory and bring about at least one of a change in a status classification and a change in a status.

2. A monitoring unit in accordance with claim 1, wherein the status calculation automatically identifies non-acquired sensor signals and generates an error message.

3. A monitoring unit in accordance with claim 1, wherein the control unit makes available to the monitoring unit at least one of a filtering function, a prioritization function a sorting function and an availability display on the availability of the sensor data acquisition interface.

4. A monitoring unit in accordance with claim 1, wherein the visualization of the results of the status calculation comprises a graphically displayed classification of a calculated status result to sepsis classes according to sepsis guidelines stored in the memory.

5. A monitoring unit in accordance with claim 1, wherein the visualization of the results of the status calculation comprises an overview display in the form of a tabular structure on the patient, wherein the overview display is a ward-overlapping display and wherein the overview display identifies a status and classifies the identified status according to guidelines implemented in the memory.

6. A monitoring unit in accordance with claim 1, wherein the status calculation comprises a patient-specific detail view structured in parameter tiles, wherein the detail view comprises all status-relevant sensor signals, wherein the parameter tile is sensor-specific and comprises a display of the sensor signal over time with visualized limit values and instances wherein limit values were exceeded besides the currently acquired sensor signals.

7. A monitoring unit in accordance with claim 1, wherein the status calculation comprises a logbook view with a measured value table of acquired sensor signals and with a status-specific trend graph.

8. A monitoring unit for the electronic monitoring of sensor signals related to sepsis monitoring, the monitoring unit comprising:
  a monitor for visualizing results of a sepsis status calculation;
  a sensor data acquisition interface acquiring status-relevant sensor signals from medical devices, the sensor signals comprising data corresponding to sepsis monitoring of a patient;
  a memory storing at least one of rules for analyzing status-relevant parameters and rules for processing status-relevant parameters and rules for sensor signals;
  a rule engine interface to the memory;
  a computer-assisted control unit comprises an arithmetic unit, wherein
  the arithmetic unit is supplied with the acquired sensor signals via the sensor data acquisition interface, the arithmetic unit determining the sepsis status calculation based on the sensor signals; and
  the computer-assisted control unit controls the visualization of the sepsis status calculation dynamically on the monitor based on the rules stored in the memory and defined for the sepsis status calculation such that the visualization of the results of the status calculation comprises a logbook view comprising a trend graph of the sensor signals over time, the logbook view comprising a display of a sepsis status of a patient based on the sepsis status calculation, the sepsis status including a degree of severity of the sepsis status, the monitor displaying the degree of severity of the sepsis status, wherein the degree of severity is determined by comparing respective predefined limit values with currently acquired sensor signals, wherein the visualization of the results of the status calculation in the display comprises an identification of sensor signal values or parameter values that do not comply with limit values stored in the memory and bring about at least one of a change in a status classification and a change in a status.

9. A monitoring unit in accordance with claim 8, wherein the status calculation automatically identifies non-acquired sensor signals and generates an error message.

10. A monitoring unit in accordance with claim 8, wherein the control unit makes available to the monitoring unit at least one of a filtering function, a prioritization function a sorting function and an availability display on the availability of the sensor data acquisition interface.

11. A monitoring unit in accordance with claim 8, wherein the visualization of the results of the status calculation comprises a graphically displayed classification of a calculated status result to sepsis classes according to sepsis guidelines stored in the memory.

12. A monitoring unit in accordance with claim 8, wherein the visualization of the results of the status calculation comprises an overview display in the form of a tabular structure on the patient, wherein the overview display is a ward-overlapping display and wherein the overview display identifies a status and classifies the identified status according to guidelines implemented in the memory.

13. A monitoring unit in accordance with claim 8, wherein the status calculation comprises a patient-specific detail view structured in parameter tiles, wherein the detail view comprises all status-relevant sensor signals, wherein the parameter tile is sensor-specific and comprises a display of the sensor signal over time with visualized limit values and instances wherein limit values were exceeded besides the currently acquired sensor signals.

14. A monitoring unit in accordance with claim 8, wherein the status calculation comprises a logbook view with a measured value table of acquired sensor signals and with a status-specific trend graph.

15. A process for the electronic monitoring of sensor signals related to sepsis monitoring, the process comprising the steps of:
  providing a knowledge base, wherein rules for an analysis and processing of status-relevant sensor signals and/or parameters are stored;
  dynamically acquiring time-discrete, status-relevant sensor signals and/or parameter values from medical devices, the sensor signals and/or parameter values comprising data associated with sepsis monitoring of a patient;
  performing a status calculation for the sensor signals and/or parameter values acquired with access to the knowledge base, wherein the status calculation comprises a curve showing all status-relevant sensor signals over time;

determining a current status from the status calculation and identifying all sensor signals and/or parameter values causing the status, the current status corresponding to a sepsis status of the patient, the sepsis status of the patient including a degree of severity of the sepsis status of the patient; and dynamically generating at least one of an interactive overview display, a detail view and an interactive logbook view, wherein the process is computer implemented, the at least one of the interactive overview display, the detail view and the interactive logbook view comprising a visualization of the sepsis status of the patient and the degree of severity of the sepsis status, wherein the degree of severity is determined by comparing respective predefined limit values with currently acquired sensor signals, wherein the visualization of the results of the status calculation in the display comprises an identification of sensor signal values or parameter values that do not comply with limit values stored in the memory and bring about at least one of a change in a status classification and a change in a status.

16. A process according to claim 15, further comprising providing a computer program product that can be loaded or is loaded into a memory of a computer with commands readable by the computer for carrying out the process steps and wherein the commands are executed on the computer, the status calculation comprising a patient-specific detail view structured in parameter tiles, wherein a graphical progression representation of a currently measured signal is displayed over time in each of the parameter tiles of the patient-specific detail view, the graphical progression representation being located adjacent to the currently measured sensor signal.

17. A process in accordance with claim 15, wherein the determination of the status is also performed when not all status-relevant sensor signals have been acquired.

18. A process for the electronic monitoring of sensor signals related to sepsis monitoring, the process comprising the steps of:

acquiring status-relevant sensor signals from medical devices by means of a sensor data acquisition interface of a monitoring unit, the sensor signals comprising data corresponding to sepsis monitoring of a patient;

supplying the arithmetic unit with at least one of rules for analyzing status-relevant parameters and rules for processing status-relevant parameters and rules for sensor signals by means of a rule engine interface of the monitoring unit to a memory and storing at least one of the rules for analyzing status-relevant parameters and the rules for processing status-relevant parameters and the rules for sensor signals in the memory;

performing a status calculation by at least one of analyzing the sensor signals and processing the sensor signals;

visualizing results of the status calculation on a monitor of the monitoring unit, wherein:

the visualization of the results of the status calculation on the monitor is carried out dynamically such that the visualization comprises a detail view structured in parameter tiles, the parameter tiles comprising a column of parameter tiles; and a display of a course of the sensor signal over time is visualized in each parameter tile of the detail view besides a currently measured sensor signal, each of the parameter tiles in the column of parameter tiles comprising a sepsis status of a patient based on the status calculation and a degree of severity of the sepsis status, wherein the degree of severity is determined by comparing respective predefined limit values with currently acquired sensor signals, wherein the display of the status calculation comprises an identification of sensor signal values or parameter values that do not comply with limit values stored in the memory and bring about at least one of a change in a status classification and a change in a status.

19. A process according to claim 18, further comprising providing a computer program product that can be loaded or is loaded into a memory of a computer with commands readable by the computer for carrying out the process steps and wherein the commands are executed on the computer, the status calculation comprising a patient-specific detail view structured in parameter tiles, wherein a graphical progression representation of a currently measured signal is displayed over time in each of the parameter tiles of the patient-specific detail view, the graphical progression representation being located adjacent to the currently measured sensor signal.

* * * * *